(12) United States Patent
Chen et al.

(10) Patent No.: US 8,293,349 B1
(45) Date of Patent: Oct. 23, 2012

(54) BALLOON FORMING PROCESS AND BALLOONS MADE THEREFROM

(75) Inventors: John Jianhua Chen, Plymouth, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1086 days.

(21) Appl. No.: 10/853,543

(22) Filed: May 24, 2004

Related U.S. Application Data

(63) Continuation of application No. 10/622,628, filed on Jul. 18, 2003, now abandoned.

(51) Int. Cl.
*A61M 31/00* (2006.01)
*A61M 37/00* (2006.01)
*B32B 1/00* (2006.01)
*B32B 1/08* (2006.01)

(52) U.S. Cl. ............ 428/36.4; 428/35.2; 428/35.3; 428/35.4; 428/35.5; 428/35.8; 428/35.9; 428/36.6; 428/36.8; 428/34.4; 428/34.6; 428/34.7; 604/103.06

(58) Field of Classification Search .......... 428/34.1, 428/34.4, 34.6, 34.7, 35.2, 35.3, 35.4, 35.5, 428/35.7, 35.8, 35.9, 36.4, 36.6, 36.7, 36.8; 604/96.01, 103.06
See application file for complete search history.

(56) References Cited

U.S. PATENT DOCUMENTS

| | | | | |
|---|---|---|---|---|
| 2,393,541 A | | 1/1946 | Kohler ............ 219/634 |
| 4,638,803 A | * | 1/1987 | Rand .............. 606/192 |
| 4,808,164 A | | 2/1989 | Hess ............... 604/95.01 |
| 4,927,413 A | | 5/1990 | Hess ............... 604/95 |
| 5,098,429 A | | 3/1992 | Sterzer ............ 606/28 |
| 5,160,396 A | | 11/1992 | Jensen et al. ........ 156/304.2 |
| 5,306,377 A | | 4/1994 | Jensen et al. ........ 156/304.2 |
| 5,348,538 A | | 9/1994 | Wang et al. .......... 604/96 |
| 5,378,879 A | | 1/1995 | Monovoukas ....... 219/634 |
| 5,429,583 A | | 7/1995 | Paulus et al. ......... 600/2 |
| 5,556,383 A | | 9/1996 | Wang et al. .......... 604/96 |
| 5,569,195 A | | 10/1996 | Saab ............... 604/103.13 |
| 5,728,079 A | | 3/1998 | Weber et al. ......... 604/280 |
| 5,799,978 A | * | 9/1998 | Grinnell ............ 281/29 |
| 5,830,182 A | | 11/1998 | Wang et al. .......... 604/96 |
| 5,838,079 A | * | 11/1998 | Morohashi et al. .... 310/12.24 |
| 5,876,743 A | * | 3/1999 | Ibsen et al. .......... 424/426 |
| 5,908,410 A | * | 6/1999 | Weber et al. ......... 604/523 |
| 5,951,941 A | | 9/1999 | Wang et al. .......... 264/523 |
| 6,056,844 A | | 5/2000 | Guiles et al. ........ 156/272.4 |
| 6,146,356 A | | 11/2000 | Wang et al. .......... 604/96 |
| 6,171,278 B1 | | 1/2001 | Wang et al. .......... 604/96 |
| 6,299,990 B1 | | 10/2001 | Watanabe et al. ...... 428/692 |
| 6,337,215 B1 | | 1/2002 | Wilson ............. 428/526 |
| 6,406,457 B1 | | 6/2002 | Wang et al. .......... 604/96.01 |
| 6,427,089 B1 | * | 7/2002 | Knowlton ........... 607/101 |
| 6,475,650 B2 | | 11/2002 | Watanabe et al. ...... 428/692 |
| 6,641,694 B1 | | 11/2003 | Lee ................. 156/244.14 |
| 6,911,017 B2 | * | 6/2005 | Lee et al. ........... 604/96.01 |
| 2003/0050692 A1 | * | 3/2003 | Sirhan et al. ........ 623/1.42 |
| 2003/0163187 A1 | | 8/2003 | Weber .............. 623/1.2 |
| 2003/0183986 A1 | | 10/2003 | Weber .............. 264/404 |
| 2004/0021249 A1 | | 2/2004 | Weber et al. ......... 264/248 |
| 2004/0104512 A1 | | 6/2004 | Eidenschink ........ 264/295 |

OTHER PUBLICATIONS 6 entries (for "iron oxide, black", "iron oxide, metallic brown", "iron oxide red", "ferric oxide", "iron oxide, brown" and "iron oxide yellow") (6 pages) from online version of Hawley's Condensed Chemical Dictionary, 14$^{th}$ Edition, © 2002, John Wiley & Sons, Inc.*

* cited by examiner

*Primary Examiner* — Walter B Aughenbaugh
(74) *Attorney, Agent, or Firm* — Vidas, Arrett & Steinkraus, P.A.

(57) ABSTRACT

A dilatation balloon formed with at least one layer, the layer including at least one polymeric material and at least one material which is a heating medium, the heating medium sensitive to an electromagnetic field.

17 Claims, No Drawings

BALLOON FORMING PROCESS AND BALLOONS MADE THEREFROM

CROSS-REFERENCE TO RELATED APPLICATIONS

This application is a continuation of U.S. patent application Ser. No. 10/622,628, filed Jul. 18, 2003, now abandoned.

BACKGROUND OF THE INVENTION

The present invention relates to balloons for angioplasty procedures and to methods of making the same.

Balloon catheters are well-known devices in which the catheter carries an inflatable balloon to occlude and seal a body space, to expand a blood vessel through pressurized inflation of the balloon, or for any other desired purpose which may typically but not necessarily be a therapeutic purpose in the medical field. In the case of dilatation balloon catheters for angioplasty, for example a PTCA procedure, the catheter balloon is generally made out of a thin, strong material which is of relatively low resilience. For example, the catheter balloon may be made out of biaxially oriented polyethylene terephthalate (PET) or a polyamide material such as nylon. Such strong, flexible materials are commonly used for angioplasty balloons, and have the advantage that they are flexible but inelastic so that they can expand outwardly to a predetermined diameter, and then cease further expansion at normal pressures, to avoid damage to the artery wall by over expansion.

Balloon formation typically involves three major steps in the process which include forming a tubular preform by extruding, injection molding dip-molding, spraying, and so forth, molding the balloon and annealing the balloon. Depending on the balloon material employed, the preform may be axially stretched before it is blown. This biaxial orientation of the material is done during the tubing expansion step. A pulling tension may or may not be employed simultaneously during the expansion step.

In a conventional balloon molding step, a tube is heated from its outside surface through the use of hot water, a heating block, or an infrared heating source, for example. Once the tube is heated to the proper balloon forming temperature beyond the softening temperature of the polymer, the balloon is then formed using pressurized air and tension.

Using the heating sources described above, however, heating gradients are created from the outside surface of the balloon where the temperature is higher, to the inside surface of the balloon where the temperature is lower. This can result in a scenario wherein the outside surface gets overheated and the inside surface is under heated. The result of such uneven heating along the cross-section of the balloon can result in premature forming and more defects, or less than optimal biaxial orientation which may be reflected in the physical characteristics of the balloon, for example, lower burst pressure and higher distention.

It is known to use induction heating technologies to weld, forge, bond or set polymer materials by mixing ferromagnetic particles in the polymer to be heated.

See for example, U.S. Pat. No. 6,056,844, which is incorporated by reference herein in its entirety.

There remains a need in the art for a balloon forming method which results in even heating of the tube during the balloon molding process which avoids detriment to the balloon characteristics.

SUMMARY OF THE INVENTION

The present invention relates to an improved method of forming balloons to affect even heating of the tubing during the balloon molding process.

More specifically, the present invention relates to the addition of a material which acts as a heating medium to the tubing material from which the balloon is formed. One example of such a material is a ferromagnetic material which desirably has a small particle size.

In the latter case, the ferromagnetic materials generate heat through hysteresis losses. Generated heat is transferred from the ferromagnetic material to the polymeric material. The amount of the ferromagnetic material added, the wall thickness of the balloon, and the particle size of the ferromagnetic particles or powder all affect the amount of heat transferred to the polymeric material.

In accordance with one aspect of the invention, a method of forming a balloon is provided. The method includes the steps of compounding at least one material which acts as a heating medium with at least one polymeric material, extruding the compounded material into tubing and molding a balloon from the extruded tubing with heating.

Examples of materials which can be employed as a heating medium include those materials which are referred to as ferrite oxides. Examplex include those having having the general formula:

$$Cr_xO_y \text{ or } Fe_xO_y$$

and alloys of these materials as well.

The balloons may be formed of any polymeric material known in the art and may be single layer balloons, as well as multi-layer balloons.

The balloon material and the heating medium may be compounded together prior to extrusion, or compounding may be accomplished during the extrusion process itself.

The method according to the present invention provides several advantages over currently used methods including, for example, more even heating of the balloon material resulting in an improved balloon. The ability to accurately control the temperature and timing of balloon formation can result in a balloon which is optimally oriented and which has improved burst pressure and distensibility, and which does not have defects such as tears, footballs or fisheyes which are small air pockets which form in the balloon wall.

The method according to the present invention eliminates the need for a water bath and consequently eliminates water vapor accumulation around the production equipment. This eliminates the need for regular water bath maintenance and pyrogen testing. The heating method according to the present invention also provides a wider temperature operating range than with the currently used water baths or jackets and allows for an essentially unlimited molding temperature range.

DETAILED DESCRIPTION OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

The balloons according to the invention are formed from at least one layer of polymeric material which forms the balloon wall which has blended, mixed, embedded, homogenized, or otherwise dispersed therein a heating medium. Other ways of dispersing the heating medium in the polymer not specifically mentioned herein may also be employed. Such examples are for illustrative purposes only, and are not seen to limit the scope of the present invention.

The balloons may be fabricated from any polymeric material known to those of skill in the art include both thermoplastics including elastomers including block copolymer elastomers, and non-elastomers, as well as thermosetting materials. Examples of useful classes of materials include, but are not limited to, polyolefins, polyesters, polyethers, polyamides and nylons, polyimides, polyketones, polyphenylene sulfides, polysulfones, polyvinyl chlorides, fluoropolymers such as ePTFE, and mixtures thereof. This also includes any copolymers and terpolymers of such materials. Hereinafter, any polymer formed from more than one monomer shall be referred to as a copolymer. Such materials are known to those of skill in the art. This list is for illustrative purposes only, and is not seen to limit the scope of the present invention.

Block copolymer elastomers are discussed in commonly assigned U.S. Pat. No. 6,406,457, U.S. Pat. No. 6,171,278, U.S. Pat. No. 6,146,356, U.S. Pat. No. 5,951,941, U.S. Pat. No. 5,830,182, U.S. Pat. No. 5,556,383, all of which are incorporated by reference herein in their entirety.

Suitable materials are described in commonly assigned U.S. Pat. No. 5,348,538, the entire content of which is incorporated by reference herein.

Intermediate compliant balloons may be formed from polyethylene (high density, medium density, low density, ultra low density) and nylon materials, for example. Typically, medium to higher density polyethylenes are more suitable for use than those of the low and ultra low density variety.

Non-compliant balloons can be formed from materials such as polyethylene terephthalate (PET), polyimides, polyamides, polyesters, polycarbonates, polyphenylene sulfides, polypropylenes, polyurethanes, and so forth. These materials are typically classified as non-compliant materials which are relatively rigid or stiff polymeric materials.

Highly compliant balloons are made from relatively soft or flexible polymeric materials. Examples of these materials are thermoplastic polymers, thermoplastic elastomers, polyethylene (ultra high molecular weight, ultra high density, high density, intermediate density, low and linear low density, ultra low density), various copolymers and blends of polyethylene, ionomers, polyesters, polyurethanes, polycarbonates, polyamides including the Nylons such as Nylon 12, polyvinyl chloride, acrylonitrile-butadiene-styrene copolymers, polyether-polyester copolymers, and polyether-polyamide copolymers. A suitable copolymer material, polyolefin material is available from E. I. DuPont de Nemours and Co. (Wilmington, Del.), under the trade name Surlyn® Ionomers.

Other polymers which may be employed in balloon forming and not specifically classified above, include, for example, polytetrafluoroethylene (PTFE), tetrafluoro ethylene (TFE), polyvinylidine fluoride (PVDF), polyethylene naphthalenedicarboxylate (PEN), and so forth. Materials such as fluoropolymers like PTFE, for example, may find utility as low friction linings or coatings, for example.

Some of the more typical materials include, for example, polyethylene terephthalate, polyamides such as nylon, polyether-block-amides (PEBAX), polyester-polyether block copolymers, and so forth. Dilatation balloons typically have at least two profiles including a noninflated profile, an inflated, non-distended working profile as well as a stretched inflated profile which is achieved by applying pressure through a dilatation catheter or the like that is in excess of that needed to achieve the inflated, non-distended profile and which is adequate to effect dilatation or the like up to a maximum pre-bursting pressure application. The maximum pre-bursting size of the balloon can be tailored depending upon the needs of the particular balloon within a wide range of possible maximum pre-bursting sizes.

The above lists are intended for illustrative purposes only and are not intended to limit the scope of the present invention. Other materials and combinations of materials not specifically discussed herein and known to those of ordinary skill in the art may also be employed herein without departing from the scope of the present invention.

The heating medium may be any material which is sensitive to application of an electromagnetic field. Examples of such materials include ferromagnetic materials. These materials may be used in the form of a particle or powder, for example and combined with the polymeric material. When exposed to an electromagnetic or induction field, the ferromagnetic particles will heat up through hysteresis losses until they reach their Curie temperature. The polymeric material is thereby heated due to hysterisis losses associated with the vibrating ferromagnetic materials as they absorb the electromagnetic radiation. Using this method, temperatures can be more accurately controlled due to the fact that hysterisis losses only occur up to the Curie temperature of the ferromagnetic material. All ferromagnets are associated with a Curie temperature which is the temperature above which the ferromagnetic material loses its ferromagnetic properties or permanent magnetism.

Thus, in one embodiment, a self-regulating control mechanism can be employed by using the Curie temperature of the ferromagnetic material. However, this is not the only method of temperature control which can be employed in the present invention. For example, the mold may be equipped with a fiber optic sensor to measure the temperature of the tube. The information can then be used to regulate the power level of the radio frequency field, or a feedback mechanism may be employed to send a message to switch the radio frequency source on and for a defined periods of time based on the temperature desired. The power level may also be controlled using the latter method.

The mold is desirably transparent when employing electromagnetic waves. Teflon may be employed, for example, if radiofrequencies are employed. Quartz or zinc selenium (ZnSe) may be employed if higher frequencies in the optical range are desirably employed. Ceramic molds (ZrO) may also be employed. Carbon black may be optionally added to the polymer to absorb radiation in the infrared region.

Using molds of this type may offer other advantages over currently employed metallic molds. Such molds are poor thermal conductors which allows them to maintain very sharp temperature transitions in the balloon wall. Also, low thermal capacities allow them temperature of the balloon to drop quickly once the electromagnetic field has been turned off because of the absence of a thermal load in the mold.

Thus, by selecting a ferromagnetic material having a Curie temperature which is similar to the balloon molding temperature, the temperature can be more accurately controlled without overheating some areas of the balloon material and underheating others. Furthermore, the electromagnetic field can pass through all polymers, heating ferromagnetic material placed on inside surfaces which enables heating both the inside and the outside. Consequently, the method according to the present invention offers advantages in making not only single layer balloon structures, but multi-layer balloon structures as well. The temperature may also be controlled by monitoring the temperature of the tube material itself and turning the field power on and off. Thus, while the Curie temperature can be employed to limit the temperature, it does not have to be the limiting factor.

The ferromagnetic material is desirably in a particulate form having a particle size of about 1 µm or less.

The ferromagnetic material may be compounded with the polymeric material similarly to the way in which any filler is compounded with a polymeric material prior to extrusion of the tubing from which the balloon is then formed, or during the extrusion process itself. Balloon preforms may be formed other than by extrusion such as by injection molding, solution casting, dip coating and so on. Therefore, the method of compounding the ferromagnetic material with the polymeric material may be tailored to fit the process employed in making the balloon preform. Any method known for compounding polymeric materials may be employed herein.

Any particulate ferromagnetic material or a powder of such a material may be employed herein. Examples of suitable ferromagnetic materials include, but are not limited to, iron, manganese, titanium, chromium, cobalt, nickel or the like, or particles or whiskers made of ferrite or an oxide which are alloys of the above-mentioned particles, or conductive particles made of carbon black or the like are mixed and dispersed the polymeric material. Ferrite oxide is employed in one particular embodiment of the present invention. Ferromagnetic materials of this type are described in U.S. Pat. No. 6,056,844, the entire content of which is incorporated by reference herein in its entirety.

Examples of specific oxides useful herein include, for example those having the formula $Fe_xO_y$, wherein Fe is used to refer generally to any ferromagnetic metal such as, for example, $Fe_3O_4$, $Fe_2O_3$, $Cr_2O_3$, $FeCr_2O_4$, and so forth. The x/y ratio can be changed by adjusting the rate of oxygen flow during the manufacture of these materials. These types of materials as well as how the materials are manufactured is described in commonly assigned copending U.S. patent application Ser. No. 10/084,857, the entire content of which is incorporated by reference herein.

The specific composition of the particles made out of the ferromagnetic materials or alloys thereof will define the Curie temperature of the resultant compound. The specific ratio of the oxides is determined by the oxygen flow during the production process of these particles. These particles can have a particle size of about 5-100 nanometers and even as low as between about 5-10 nanometers. Particles having such small particle size may be referred to as nano-particles.

Also, as described in U.S. Pat. No. 5,429,583, incorporated by reference herein in its entirety, alloys of palladium-cobalt can be made with a very sharp Curie transition temperatures within a large range of temperatures which can be tailored as desired by varying the percentage of each element in the alloy.

Alternatively, conducting elements may be incorporated into the polymeric material through embedding, mixing, blending, extruding, or otherwise dispersing the conducting elements in the polymeric material. Upon application of a current through the tube, the tube will be heated through resistance losses of the conducting elements. Carbon black, carbon nanotubes, thin embedded stripes made out of a conductive polymer such as polyalinine or polypyrrole, may also be employed. Using such conducting elements, the heating process may be controlled by measuring the temperature dependent resistance of the conducting tube.

During the molding process, heat may be imparted to the tubing from which the balloon is formed within the molding chamber thereby thermoforming the balloon with heat setting. Heat setting typically involves raising the temperature of the balloon while it is under inflated stress and holding it at that temperature for a specified amount of time. A typical molding process may, for example, involve molding at a temperature of no more than about 95° C. The temperature is first raised to about 65° C. at which point the pressure is increased to about 250 psi to blow the balloon. Once the temperature reaches about 95° C., it will be held there for a time such as about 30 seconds in order to heat set the balloon. An advantage of the present invention is that it allows for more flexibility and a wider temperature range during molding, and also allows for a higher maximum temperature as well.

Thereafter, the heated fluid within the fluid jacket may be exchanged for cooling fluid in order to substantially maintain the size and shape of the balloon formed within the molding chamber. After the pressure has been relieved, the balloon may be removed from the apparatus.

The method according to the present invention provides other advantages in that the balloons formed according to the present method also exhibit more controlled distensibility at high pressures whereby expansion beyond the working or fully expanded but non-distended dilation profile of the balloon is possible.

The method of the present invention allows for a variety of polymeric materials to be employed, even those which have different heating requirements. Different combinations of ferromagnetic particles or different concentrations thereof may be employed in the polymeric composition as well in order to impart different heating characteristics. For example, employing different concentrations of ferromagnetic materials along the axial direction of a tube can provide a gradient of heating along the axial direction. Employing different ferromagnetic particles along the axial direction can result in a different heating rate or different heating level upon application of a radio frequency field. Intermittent extrusion may be employed in order to provide different combinations of polymers and/or different combinations of ferromagnetic particles in different locations of a device. Different polymers may be employed having different concentrations of the ferromagnetic material as well in order to provide differential heating or to compensate for different heating requirements required by different polymers or combinations thereof.

The present invention therefore allows for the manufacture of balloons using multiple polymers requiring different heating rates which may not otherwise be used together. Thus, two or more components may be formed from different polymers and/or different ferromagnetic materials may be made using injection molding, intermittent extrusion, coextrusion, and so forth.

The electromagnetic field can be created using any means or apparatus known in the art. One method is to employ an anode and a cathode to create the magnetic field. Other methods of creating a field include the use of microwaves in the range of about 915 MHz and 2.45 GHz, coils or antennas, lasers, lamps, and so forth. Lasers and lamps may be selected based on the wavelength desired. For example, an incandescent lamp may be selected or a $CO_2$ laser may be selected if wavelengths in the optical frequency range are desired, or a lamp may be fluorescent or infrared, for example, as well. Other methods not specifically described herein are known to those of skill in the art and may be employed as well. These are intended for illustrative purposes only, and are not intended to limit the scope of the present invention.

As discussed above, single layer as well as multi-layer balloons may be formed according to the present invention. In the formation of multi-layer balloon structures, it may be advantageous to compound an intermediate polymeric layer which includes the material which acts as a heating medium, and outer polymeric layers having no heating medium material.

An alternative type of structure is one in which intermediate minor layers are compounded in between major polymeric layers which include no heating medium material.

The heating medium material may be placed unevenly, for example, segment heating, along the tube as well such that different areas of the balloon can be heated differently during formation. For example, cone and waist areas may be desirably heated to a higher temperature than the body portion, and the cone may be heated to a different temperature than the waist portion as well.

The above disclosure is intended to be illustrative and not exhaustive. The description will suggest many variations and alternatives to those of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A multilayer dilatation balloon formed with a structural layer wherein the balloon wall is formed from at least one polymeric material and at least one material which is a heating medium, said heating medium sensitive to an electromagnetic field and said heating medium having a Curie temperature of at least about 65° C. but no more than the molding temperature of the balloon, said structural layer is an inner balloon layer, the multilayer dilatation balloon comprising an outer layer that is heating medium-free.

2. The dilatation balloon of claim 1 wherein said at least one material which is a heating medium is a ferromagnetic material in thermoparticulate or powder form.

3. The dilatation balloon of claim 2 wherein said ferromagnetic material comprises at least one member selected from the group consisting of iron, manganese, titanium, chromium, palladium, cobalt, nickel, oxides thereof, alloys thereof, and mixtures thereof.

4. The dilatation balloon of claim 2 wherein said ferromagnetic material comprises at least one ferrite oxide.

5. The dilatation balloon of claim 4 wherein said at least one ferrite oxide has the formula $Fe_xO_y$, $Cr_xO_y$ or is an oxide of an alloy of iron and chromium.

6. A multilayer dilatation balloon formed from at least two layers including at least one first layer formed from a first composition and at least one second layer formed from a second composition which is different from said first composition, said second composition comprising at least one polymeric material and at least one heating medium, said heating medium being ferromagnetic, and said heating medium having a Curie temperature of at least about 65° C. but no more than the molding temperature of the balloon, and said first composition is free of said heating medium, said second composition forms an inner balloon structural layer and said first composition forms an outer layer.

7. The dilatation balloon of claim 6 wherein said dilatation balloon has a third layer wherein said second layer is between said first layer and said third layer, said third layer is free of heating medium.

8. The dilatation balloon of claim 1 wherein said polymeric material is selected from the group consisting of polyolefins, polyesters, polyethers, polyamides, polyimides, polyphenylene sulfides, polysulfones, polyketones, polyvinyl chlorides, copolymers and terpolymers thereof, and mixtures thereof.

9. The dilatation balloon of claim 1 wherein said polymeric material is selected from the group consisting of polyethylene, polyethylene terephthalate, polyether-block-amide, elastomeric polyesters, nylon, and mixtures thereof.

10. A dilatation balloon, formed by a method comprising the steps of
   a) compounding an inner balloon layer of at least one material which acts as a heating medium with at least one polymeric material, said at least one polymer material comprises at least one member selected from the group consisting of polyolefins, polyesters, polyethers, polyamides, polyimides, polyphenylene sulfides, polysulfones, polyketones, polyvinyl chlorides, copolymers and terpolymers thereof and mixtures thereof, said heating medium being ferromagnetic;
   b) forming the compounded material into tubing;
   c) raising the temperature of the formed tubing by applying at least one energy source which acts on said heating medium; and
   d) molding a balloon from the tubing at an elevated temperature during or directly after heating of the tube;
   wherein said heating medium is in the form of particles having a particle size of about 1 micron or less and said heating medium having a Curie temperature of at least about 65° C. but no more than the molding temperature of the balloon.

11. The dilatation balloon of claim 10 wherein said heating medium is in the form of particles having a particle size of less than 1 micron.

12. The dilatation balloon of claim 10 wherein said heating medium is a ferromagnetic material having a Curie temperature similar to the elevated temperature at which said balloon is molded.

13. The dilatation balloon of claim 10 wherein the temperature of the tubing is raised through resistance losses of the heating medium.

14. The dilatation balloon of claim 10 wherein the temperature of the tubing is raised through hysterisis losses of the heating medium.

15. The dilatation balloon of claim 7 wherein said at least one first composition comprises at least one polymeric material.

16. A single layer dilatation balloon formed with a structural layer comprising at least one polymeric material and at least one material which is a heating medium, said heating medium sensitive to an electromagnetic field and said heating medium having a Curie temperature of at least about 65° C. but no more than the molding temperature of the balloon.

17. A dilatation balloon formed with at least one layer, said at least one layer comprising at least one polymeric material and at least one material which is a heating medium, said heating medium sensitive to an electromagnetic field and said heating medium having a Curie temperature of at least about 65° C. but no more than the molding temperature of the balloon.

* * * * *